United States Patent
Steckel et al.

(10) Patent No.: US 6,362,355 B1
(45) Date of Patent: Mar. 26, 2002

(54) MOLYBDATED DISPERSANTS FROM HETEROPOLY ACIDS

(75) Inventors: Thomas F. Steckel, Chagrin Falls; Ping Y. Zhu, Solon, both of OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/489,297

(22) Filed: Jan. 21, 2000

(51) Int. Cl.$^7$ ............... C07F 11/00; C07F 9/02; C09K 3/00
(52) U.S. Cl. ............... 556/17; 556/10; 556/24; 556/57; 252/363.5
(58) Field of Search ............... 556/10, 17, 24, 556/57; 252/363.5

(56) References Cited

U.S. PATENT DOCUMENTS

| | | | |
|---|---|---|---|
| 3,290,245 A | 12/1966 | Elliott et al. | 252/32.7 |
| 3,346,604 A | 10/1967 | Roberts et al. | 260/429 |
| 4,780,553 A | 10/1988 | Suzuki et al. | 556/26 |
| 4,956,483 A | 9/1990 | Corcoran et al. | 556/26 |
| 5,319,119 A | 6/1994 | Kaneshima et al. | 556/14 |

FOREIGN PATENT DOCUMENTS

| | | |
|---|---|---|
| CA | 623 155 | 7/1961 |
| GB | 1085903 | 11/1964 |
| GB | 2 053 267 | 2/1981 |
| GB | 2 064 548 | 6/1981 |

*Primary Examiner*—Porfirio Nazario-Gonzalez
(74) *Attorney, Agent, or Firm*—David M. Shold; Michael F. Esposito

(57) ABSTRACT

A molybdated dispersant composition represented by the formula:

$$(R^1—NR^2R^3H^+)_{m-n}X_n(MoHPA)^{m-}$$

provides good friction properties to lubricants. In the formula, $R^1—NR^2R^3$ represents an amine-containing dispersant, $R^1$ is a group providing dispersant properties to said dispersant composition, each of $R^2$ and $R^3$ is independently hydrogen, a hydrocarbyl group, or an additional $R^1$ group; X is hydrogen, a monovalent metal ion, a single valence of a polyvalent metal ion, an ammonium ion, or an amine cation, m is 3 or 4, n is 0 to about 2.5 when m is 3 and 0 to about 3.5 when m is 4, and $(MoHPA)^{m-}$ is a molybdenum heteropolyacid anion of charge m.

29 Claims, No Drawings

MOLYBDATED DISPERSANTS FROM HETEROPOLY ACIDS

BACKGROUND OF THE INVENTION

The present invention relates to molybdated dispersants suitable for use as lubricant additives, and a method for their preparation.

Current engine lubrication technology requires ever-improving performance of the lubricant in order to assure adequate lubrication of demanding engines. It is known that the presence of molybdenum compounds can in many instances provide improvements in anti-wear performance and, in particular, friction reduction and, as a consequence, fuel economy. However, many molybdenum compounds are expensive or difficult to provide in a suitably oil-soluble form.

Canadian Patent 623,155, Jul. 4, 1961, discloses lubricant additives containing molybdenum compounds. Phosphomolybdic acid is reacted with an organic nitrogen base and reduced by reaction with an organic compound to a form in which at least a part of the Mo is tetravalent. The resulting product has improved solubility. Suitable nitrogen bases include (in the claims) hydrocarbon acyl amines. All known organic nitrogen bases that are soluble in or at least compatible with liquid lubricants are said to be suitable for use in neutralizing and reducing phosphomolybdic acid and for neutralizing and enhancing the thermal stability of an acidic reaction product of phosphomolybdic acid with a non-basic reducing agent. The final reaction products are said to be useful as lubricant additives.

U.S. Pat. No. 5,319,119, Kaneshima et al., Jun. 7, 1994, discloses oleophilic molybdenum compounds comprising an aliphatic amine group and a heteropolyanion group. The oleophilic molybdenum compound is a catalyst precursor capable of being changed to a catalyst having excellent catalytic activity. The catalyst can be prepared by reacting an aliphatic amine with a heteropolyacid in a hydrocarbon oil. Lubricating oil is disclosed as an illustrative hydrocarbon oil.

The present invention, therefore, solves the problem of improving lubricant performance, particularly in terms of friction reduction, in an economical manner by providing oil-soluble molybdenum compositions which can be prepared by a convenient route.

SUMMARY OF THE INVENTION

The present invention provides a molybdated dispersant composition prepared by reacting phosphoric acid or silicic acid, $MoO_3$, and an amine-containing dispersant. Otherwise stated, it provides a molybdated dispersant composition represented by the formula:

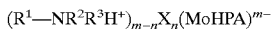

wherein $R^1$—$NR^2R^3$ represents the amine-containing dispersant, $R^1$ is a group providing dispersant properties to said dispersant composition, each of $R^2$ and $R^3$ is independently hydrogen, a hydrocarbyl group, or an additional $R^1$ group; X is hydrogen, a monovalent metal ion, a single valence of a polyvalent metal ion, an ammonium ion, or an amine cation, m is 3 or 4, n is 0 to 2.5 when m is 3 and 0 to 3.5 when m is 4, and $(MoHPA)^{m-}$ is a molybdenum heteropolyacid anion of charge m.

The invention similarly provides a process for preparing a molybdated composition comprising reacting phosphoric acid or silicic acid with $MoO_3$ and with an amine, such as an amine-containing dispersant.

The invention further provides a lubricant composition comprising a major amount of an oil of lubricating viscosity and such a molybdated dispersant, or a concentrate thereof.

DETAILED DESCRIPTION OF THE INVENTION

Various preferred features and embodiments will be described below by way of non-limiting illustration.

The present invention provides a molybdated dispersant composition. It is believed that the molybdated dispersant has, at least in part, a composition or structure which can be reasonably represented by the formula:

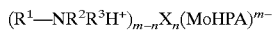

In this formula, $R^1$—$NR^2R^3$ represents an amine-containing dispersant in which $R^1$ is a group providing dispersant properties to said dispersant composition. That is, $R^1$, or a portion of $R^1$, is a group which provides sufficient solubility properties to the molybdenum-containing composition set forth above so that it can be readily dispersed or dissolved in oil. Thus, the entire moiety $R^1$—$NR^2R^3$ can be considered to be a dispersant, and it generally comprises a relatively less polar $R^1$ group, together with a generally more polar $NR^2R^3$ portion, both groups together serving to provide the dispersant properties. The more polar portion, or head, serves to interact with polar substances, which ordinarily would be dirt or contaminant particles; but for the purposes of the present invention, it interacts with the molybdenum heteropolyacid. The less polar portion provides oil solubility to permit the compound or complex to be dissolved or dispersed in oil. It is possible that an R1 group also contains additional amine groups, which may be considered to be a part of the polar "head" of the dispersant, provided that at least a portion of an R1 group is a suitably non-polar moiety. Indeed, some of the additional amine groups which may be present in R1 may form additional salt structures or otherwise interact with additional molybdenum heteropolyacids to form more complicated structures such as:

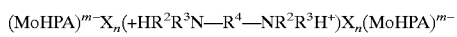

(ignoring for the purpose of illustration the stoichiometry of the structure) where $R^4$ is a linking group such as a straight chain or branched alkylene group, and the other terms are as described below.

In the formula $(R^1—NR^2R^3H^+)_{m-n}X_n(MoHPA)^{m-}$, each of $R^2$ and $R^3$ is independently hydrogen, a hydrocarbyl group, or an additional R1 group as defined above. That is, $R^2$ or $R^3$ may also provide dispersant properties to the complex.

Amine-containing dispersants in general can include acylated amines, amine-containing carboxylic esters, Mannich reaction products, hydrocarbyl substituted amines, and mixtures thereof.

Acylated amine dispersants include reaction products of one or more carboxylic acylating agent and one or more amine. The carboxylic acylating agents include C8–30 fatty acids, C14–20 isoaliphatic acids, and hydrocarbyl substituted carboxylic acylating agents. Dimer acids are described in U.S. Pat. Nos. 2,482,760, 2,482,761, 2,731,481, 2,793, 219, 2,964,545, 2,978,468, 3,157,681, and 3,256,304. The addition carboxylic acylating agents are addition (4+2 and 2+2) products of an unsaturated fatty acid with one or more unsaturated carboxylic reagents. These acids are taught in U.S. Pat. No. No. 2,444,328. In another embodiment, the carboxylic acylating agent is a hydrocarbyl substituted carboxylic acylating agent. The hydrocarbyl substituted carboxylic acylating agents are prepared by a reaction of one or more of olefins or polyalkenes with one or more of unsaturated carboxylic agents, such as itaconic, citraconic, or maleic acylating agents, typically at a temperature of 160°, or 185° C. up to 240° C., or to 210° C. Maleic acylating agents are the preferred unsaturated acylating agent. The procedures for preparing the acylating agents are well known to those skilled in the art and have been described for example in U.S. Pat. No. 3,412,111; and Ben et al., "The Ene Reaction of Maleic Anhydride With Alkenes", J. C. S. Perkin II (1977), pages 535–537. A preferred acylating agent is a hydrocarbyl-substituted succinic anhydride or the reactive equivalent thereof (e.g., an acid, acid halide, half ester). The hydrocarbyl substituent thereon is, in a preferred embodiment, a polymer of isobutylene having a number average molecular weight of 500 to 5000, preferably 900 to 3500.

The amines which react with the acylating agents may be known amines, and in the present instance a polyamine, such that at least one amine functionality can remain unacylated and available for reaction to form the molybdated dispersant of the present invention. Polyamines include aliphatic, cycloaliphatic, heterocyclic or aromatic polyamines and alkylene polyamines, condensed polyamines, hydroxy containing polyamines, arylpolyamines, and heterocyclic polyamines.

Alkylene polyamines are represented by the formula

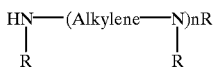

wherein n has an average value from 1 or 2 to 10, or to 7, or to 5, and the "Alkylene" group has from 1 or 2 to 10, or to 6, or to 4 carbon atoms. Each R is independently hydrogen, or an aliphatic or hydroxy-substituted aliphatic group of up to 30 carbon atoms. Acylated amines, their intermediates and methods for preparing the same are described in U.S. Pat. Nos. 3,219,666; 4,234,435; 4,952,328; 4,938,881; 4,957,649; 4,904,401; and 5,053,152.

In a preferred embodiment, the relative amounts of the amine and of the hydrocarbyl-substituted succinic anhydride which are reacted are such that the mole ratio of carbonyl groups to nitrogen atoms in the resulting succinimide dispersant is about 0.4:1 to 1.5:1, and preferably 0.7:1 to 1.4:1.

In another embodiment, the dispersant can be a carboxylic ester, provided that it also contains an amino group. The carboxylic ester is prepared by reacting one or more carboxylic acylating agents, preferably a hydrocarbyl substituted carboxylic acylating agent, with at least one organic hydroxy compound and optionally an amine. The hydroxy compound may be an alcohol (if an amine is also used) or a hydroxy containing amine.

The alcohols may contain non-hydrocarbon substituents of a type which do not interfere with the reaction of the alcohols with the acid (or other acylating agent) to form the ester. In one embodiment, the alcohols can be polyhydric alcohols, such as alkylene polyols.

Carboxylic ester dispersants may be prepared by any of several known methods. A preferred method involves the reaction of the carboxylic acylating agents described above with one or more alcohol or phenol in ratios 0.5 equivalent to 4 equivalents of hydroxy compound per equivalent of acylating agent, as described in U.S. Pat. Nos. 3,522,179 and 4,234,435. The carboxylic ester dispersants may be further reacted with at least one amine such as those described above, in order to provide the required amine functionality.

Suitable amines include polyethylenepolyamines, condensed polyamines (i.e., acid catalyzed condensation products of amine reactants with hydroxy alkyl or hydroxy aryl reactants as taught in U.S. Pat. No. 5,053,152), or heterocyclic amines, such as aminopropylmopholine. The amine can be added in an amount sufficient to react with any non-esterified carboxyl groups, while retaining amine functionality to react with the molybdenum heteropolyacid. In one embodiment, the carboxylic ester dispersants are prepared by reacting from 1 to 2 equivalents, or from 1.0 to 1.8 equivalents of hydroxy compounds, and up to 0.3 equivalent, or from 0.02 to 0.25 equivalent of polyamine per equivalent of acylating agent. The carboxylic acid acylating agent may be reacted simultaneously with both the hydroxy compound and the amine. There is generally at least 0.01 equivalent of the alcohol and at least 0.01 equivalent of the amine although the total amount of equivalents of the combination should be at least 0.5 equivalent per equivalent of acylating agent. These carboxylic ester dispersant compositions are known in the art, and the preparation of a number of these derivatives is described in, for example, U.S. Pat. Nos. 3,957,854 and 4,234,435.

In another embodiment, the dispersant may simply be a hydrocarbyl-substituted amine. Hydrocarbyl-substituted amines are well known to those skilled in the art. These amines and methods for their preparation are disclosed in U.S. Pat. Nos. 3,275,554; 3,438,757; 3,454,555; 3,565,804; 3,755,433; and 3,822,289. Typically, hydrocarbyl substituted amines are prepared by reacting olefins and olefin polymers, including the above polyalkenes and halogenated derivatives thereof, with amines (mono- or polyamines). The amines may be any of the amines described above, preferably an alkylenepolyamine. Examples of hydrocarbyl substituted amines include ethylenepolyamines such as diethylene-triamine; poly(propylene)amine; N,N-dimethyl-N-poly(ethylene/propylene)-amine, (50:50 mole ratio of monomers); polybutene amine; N,N-di(hydroxy-ethyl)-N-polybutene amine; N-(2-hydroxypropyl)-N-polybutene amine; N-poly-butene -aniline; N-polybutenemorpholine; N-poly(butene)ethylenediamine; N-poly (propylene) trimethylenediamine; N-poly(butene)diethylenetriamine; N',N'-poly (butene)tetraethylenepentamine; and N,N-dimethyl-N'-poly(propylene)-1,3-propylenediamine. Similar molybdated compositions can be prepared by the reaction (described in greater detail below), of phosphoric or silicic acid, MoO3, and an amine, even if the amine is not specifically a dispersant.

In another embodiment, the dispersant can be a Mannich dispersant. Mannich dispersants are generally formed by the reaction of at least one aldehyde, such as formaldehyde and paraformaldehyde, at least one of the above described amines, preferably a polyamine, such as a polyalkylenepolyamine, and at least one alkyl substituted hydroxyaromatic compound. The amounts of the reagents is such that the molar ratio of hydroxyaromatic compound to formaldehyde to amine is in the range from (1:1:1) to (1:3:3). The hydroxyaromatic compound is generally an alkyl substituted hydroxyaromatic compound. This term includes the above described phenols. The hydroxyaromatic compounds are those substituted with at least one, and preferably not more than two, aliphatic or alicyclic groups having from 6 to 400, or from 30 to 300, or from 50 to 200 carbon atoms. These groups may be derived from one or more of the above described olefins or polyalkenes. In one embodiment, the hydroxyaromatic compound is a phenol substituted with an aliphatic or alicyclic hydrocarbon-based group having an $\overline{M}n$ of 420 to 10,000. Mannich dispersants are described in the following patents. U.S. Pat. Nos. 3,980,569; 3,877,899; and 4,454,059.

Dispersants can also be treated by or reacted with a variety of agents to produce well-known variants. Such agent include sulfurizing agents such as elemental sulfur or CS2 and dimercaptothiadizoles. Reactions of dispersants with a dimercaptothiadiazole is taught, for example, in U.S. Patent No. 4,136,043.

In the formulas given above, the heteropolyacid anion $(MoHPA)^{m-}$ is not necessarily completely neutralized by the amine-containing dispersant. This fact is represented by the optional presence in the formula of X, which can be hydrogen, a monovalent metal ion, a single valence of a polyvalent metal ion, an ammonium ion, or an amine cation from a source other than a dispersant, or mixtures of the above. The amount of X present in a given structure is that amount which, together with the ion from the dispersant, is sufficient to satisfy the valence or charge of the molybdenum heteropolyacid. The valence of the heteropolyacid, represented by m, is typically 3 or 4: 3 when it is a phosphorus based material and 4 when it is a silica based material. The amount of X, represented by n, is typically 0 to 2.5 when m is 3 and 0 to 3.5 when m is 4. Preferably X is hydrogen. In a preferred embodiment, n is zero, that is, there is substantially no X in the composition.

Molybdenum containing heteropolyacids and their corresponding anions, represented herein by $(MoHPA)^{m-}$, are well known materials. Heteropolyanions are polymeric oxoanions formed by a condensation reaction of two or more different oxoanions, e.g., $$12MoO_4^{2-} + HPO_4^{2-} + 23\ H^+ \rightarrow (PMo_{12}O_{40})^{3-} + 12H_2O$$

Formation of the corresponding heteropoly acid is simply the reaction:

$$12MoO_3 + H_3PO_4 \rightarrow H_3PMo_{12}O_{40}.$$

A similar reaction can be written with silicic acid:

$$12MoO_3 + H_4SiO_4 \rightarrow H_4SiMo_{12}O_{40}$$

forming silicomolybdic acid, the anion of which can have a charge of 4–.

A variety of structures are known for these materials; they can have, for instance, the so-called Keggin structure, wherein twelve $MoO_6$ octahedra surround a central $PO_4$ tetrahedron (in the case where phosphorus is employed). Other structures and related formulas are also known, including $PMo_{12}O_{40}^{6-}$, $PMo_{18}O_{62}^{6-}$, $P_2Mo_5O_{23}^{4-}$, $PMo_9O_{34}^{9-}$, $P_2Mo_{18}O_{62}^{6-}$, $PMo_{11}O_{39}^{7-}$, $PMo_9W_3O_{40}^{3-}$, $GeMo_{12}O_{40}^{4-}$, $SiMo_3W_9O_{40}^{5-}$, and $TeMo_6O_{24}^{6-}$, where P, Ge, Si, or Te and Mo or W are taken as representative elements and the indicated structure is an ion with the appropriate charge. The central atom of the Keggin structure, which is typically phosphorus, as shown, can also be any of the Group IIIA to Group VIIA (ACS numbering) metalloids or non-transition metals, including P, As, Si, Ge, B, Al, Sb, and Te. The molybdenum (Mo) in the above formula fills the role known as the "poly atom," which can in general be any of the Group VB or VIB transition metals, including W, V, Cr, Nb, Mo, or Ta, although of course for the present invention molybdenum is desired. Thus suitable materials include preferably phosphomolybdates and silicomolybdates. Other combinations selected from among the above elements are also possible, including arsenomolybdates, teluromolybdates, and aluminomolybdates, and phosphovanadylmolybdates, the latter representing a mixed material having a formula (for the anion portion) of $PV_2Mo_{10}O_{40}^{5-}$. The preferred material is a phosphomolybdate, which term generally encompasses both the acid and the various salts, described below. The preferred species of the $(MoHPA)^3$ is $PMo_{12}O_{40}^{3-}$.

For more detailed information on the structures of heteropolyacid materials, attention is directed to *Chemical Reviews*, January/February 1998, Vol. 98 (No. 1) and Misono, "Heterogeneous Catalysis by Heteropoly Compounds of Molybdenum and Tungsten," Catal. Rev.-Sci. Eng., 29(2&3), 269–321 (1987), in particular, pages 270–27 and 278–280. In the present invention, the hydrogen ions have been partially or fully replaced by a dispersant anion, $R^1$—$NR^2R^3H^+$ as described above, that is, the heteropolyacid is a partially or fully neutralized salt of the heteropolyacid.

Heteropoly acids are commercially available materials, (e.g., Aldrich Chemical Company, #22,420-0 and 38,336-8). The salts are similarly commercially available. Alternatively, they can be prepared from the acid materials by neutralization with an appropriate amount of base. Heteropoly acids are generally received in a hydrated form. They can be employed in this form (uncalcined) or they can be treated (calcined) to remove some or all of the water of hydration, that is, to provide a dehydrated or otherwise modified species.

It is difficult or impossible to determine precisely the structural form in which the molybdated dispersants of the present invention exist. It is believed that the molybdenum atoms in the composition of the present invention predominantly or entirely retain the +6 oxidation state. While it is believed that at least a portion, and probably a substantial portion, of the molybdated dispersants exhibit the heteropoly acid type structures as set forth above, this has not been unambiguously determined. The present invention is therefore intended to encompass other related structures that may be formed. Accordingly, the molybdated dispersants are also described by their various methods of preparation.

One way by which the molybdated dispersants of the present invention can be prepared is by mixing an amine-containing dispersant with a molybdenum heteropolyacid (or a partially neutralized salt thereof) and permitting the neutralization reaction to occur to form the desired salt. Since many dispersants are commercially available as a solution with 40–60% diluent oil, the diluent oil can provide a convenient medium in which the reaction is run. For efficient reaction, it is preferred that the molybdenum heteropolyacid be supplied to the reaction mixture as a solution of preferably 10–50% by weight (more preferably 20–30% by weight) of the heteropolyacid in a lower alkanol, that is, containing up to 3 or 4 carbon atoms, such as ethanol or, preferably, methanol. The alcohol preferably contains no more than a minor amount of water.

EXAMPLE A

A 500 mL 4-neck round bottom flask is equipped with an overhead mechanical stirrer, an addition funnel, a temperature controller, and a condenser. The flask is charged with 250 g of succinimide dispersant made from 1000 molecular weight polyisobutylene. To the addition funnel is added a solution of 5 g of $H_3PMo_{12}O_{40}xH_2O$ in 15 g methanol. The contents of the addition funnel are added dropwise to the reaction flask over 20 minutes. At the end of the addition, the temperature has increased to 51° C. The reaction mixture is slowly heated to about 120° C. over 2 hours to remove the methanol. The mixture is further stripped under vacuum to remove the remaining volatile components. The resulting material is diluted with 100 g diluent oil and filtered through a pad of filter aid to yield about 285 g of dark green product containing about 0.58% Mo, 0.11% S, and 1.51% N by analysis.

The molybdenum heteropolyacid adduct can also be prepared in situ by mixing the appropriate reactants, such as molybdenum trioxide and phosphoric acid or silicic acid, as outlined above. The dispersant (or other amine) can be included in the mixture, that is, all three components can be reacted simultaneously by mixing the reactants in an inert medium such as diluent oil. It will not be necessary to isolate the intermediate molybdenum heteropoly acid. Since water appears to be a catalyst for this reaction, it is preferred that at least a catalytic amount of water be present at the time of. reaction. In practice, a catalytic amount of water will preferably be at least 1% based on dispersant plus diluent oil, more preferably 2 to 10%. Larger amounts of water can also be present, but preferably no more than 20% or 15% water will be present, since larger amounts are not necessary and the removal (stripping) time will be correspondingly increased. In order to retain an effective amount of water to catalyze the reaction, the process is preferably conducted below the normal boiling point of water, e.g., 50 or 80 to 99 or 95° C., or at the boiling point of water, under reflux conditions. Typically a temperature such as 98° C. is maintained for a period of time such as 0.5 to 24, 15, 10, or 5 hours, that is, until the reaction appears to be substantially complete. Thereafter the temperature can be raised above the boiling point of water, such as to 120 to 180° C., typically about 150° C., to remove the water and any other volatile materials. It is also possible to begin stripping of the water earlier or at a lower temperature. The product obtained can be purified by filtration if desired; the product remains dissolved in the filtrate.

The relative amounts of the $MoO_3$ and the phosphoric (or silicic) acid should normally be in their stoichiometric amounts as shown in the above formulas. However, a modest excess of one reactant or the other will not substantially harm the product. Likewise, the amount of the dispersant or other amine is not particularly critical. However, if a reactant with multiple reactive amino groups is used, it is desirable to avoid using exact stoichiometrically equivalent amount, so as to avoid formation of polymeric species. Desirably, an equivalent excess of the amine compound is used. For instance, a 4 to 8-fold excess (i.e., 12–24 basic nitrogens per P atom) can be used in the case of more viscous dispersants.

EXAMPLE B

To a flask equipped with a stirrer, thermowell, and reflux condenser is charged 1613 g of an amine containing dispersant. The dispersant is a hydrocarbyl succinimide dispersant having a carbonyl:nitrogen mole ratio of 6:5; the hydrocarbyl group is a polyisobutene group having a number average molecular weight of about 2000. The dispersant composition contains about 55 weight percent diluent oil and has a total base number of 15. Also added to the flask is 200 g of additional diluent oil. The mixture is heated to 90° C., and over a period of about ½ hour there is added 3.23 g of 85% phosphoric acid, 55 g of water (in addition to that present in the phosphoric acid), and 48.6 g $MoO_3$. The mixture is held, with stirring at 98–99° C. for about 17 hours, during which time the appearance of the mixture changes from hazy and muddy looking to dark blue-green and clear. The temperature is increased to 150° C, and when the temperature is reached a gentle subsurface flow of nitrogen is begun. These conditions are maintained for 5 hours to assure complete removal of water. The temperature is decreased to 130° C. and the product is filtered using a filter aid.

The molybdated dispersants of the present invention are useful as additive for lubricants, in particular engine oils. A final formulation containing the present dispersants can contain molybdenum in any desired concentration ranges, typically 0.005 or 0.01 to 0.5 or 0.1 percent by weight, preferably 0.02 to 0.08 percent by weight (i.e., 200 to 800 parts per million, or about 500 parts per million). The balance of the formulation will typically be an oil of lubricating viscosity and other typical additives for engine oils.

Oils of lubricating viscosity include natural or synthetic lubricating oils and mixtures thereof. Natural oils include animal oils, vegetable oils, mineral lubricating oils of paraffinic, naphthenic, or mixed types, solvent or acid treated mineral oils, and oils derived from coal or shale. Synthetic lubricating oils include hydrocarbon oils, halo-substituted hydrocarbon oils, alkylene oxide polymers (including those made by polymerization of ethylene oxide or propylene oxide), esters of dicarboxylic acids and a variety of alcohols including polyols, esters of monocarboxylic acids and polyols, esters of phosphorus-containing acids, polymeric tetrahydrofurans, and silicon-based oils (including siloxane oils and silicate oils). Included are unrefined, refined, and rerefined oils. Specific examples of the oils of lubricating viscosity are described in U.S. Pat. No. 4,326,972.

The lubricating oil in the invention will normally comprise the major amount of the composition. Thus it will normally be at least 50% by weight of the composition, preferably about 83 to about 98%, and most preferably about 88 to about 90%. As an alternative embodiment, however, the present invention can provide an additive concentrate in which the amount of oil is reduced. Typically the amount of oil can be 10 to 80% by weight, preferably 30 to 60%, and the amount of the molybdated dispersant is correspondingly increased. Molybdated dispersants can be prepared in a volatile medium such as toluene, rather than diluent oil, and compositions containing relatively higher amounts of active component, including diluent-free compositions, can thereby be prepared. Similarly, other additives may be present in amounts which are higher than would normally be employed in a finished lubricant. In a concentrate, the concentration of dispersant can be, for example, 5 to 20 times, or approximately 10 times the concentration in a fully formulated fluid, so that the amount of Mo is 0.1 to 1 percent by weight, and so on as above.

Lubricants for internal combustion engines generally include other additives such as detergents, viscosity index modifiers, pour point depressants, antioxidants, rust inhibitors, anticorrosion agents, and antiwear agents. Detergents are neutral or, more often basic metal salts of oil-soluble acidic materials. Overbased salts are generally single phase, homogeneous Newtonian systems characterized by a metal content in excess of that which would be present for neutralization according to the stoichiometry of the metal and the particular acidic organic compound reacted with the metal. The overbased materials are prepared by reacting an acidic material (typically an inorganic acid or lower carboxylic acid, preferably carbon dioxide) with a mixture comprising an acidic organic compound, a reaction medium comprising at least one inert, organic solvent (such as mineral oil, naphtha, toluene, or xylene) for said acidic organic material, a stoichiometric excess of a metal base, and a promoter such as a phenol or alcohol. The acidic organic material will normally have a sufficient number of carbon atoms to provide a degree of solubility in oil. Overbased materials are well known to those skilled in the art. Patents describing techniques for making basic salts of sulfonic acids, carboxylic acids, phenols, phosphonic acids, and mixtures of any two or more of these include U.S. Pat. Nos. 2,501,731; 2,616,905; 2,616,911; 2,616,925; 2,777,874; 3,256,186; 3,384,585; 3,365,396; 3,320,162; 3,318,809; 3,488,284; and 3,629,109.

Viscosity improvers are well-known polymeric materials which are used to improve the viscosity index of an oil. They include but are not limited to polyisobutenes, polymethyacrylate acid esters, polyacrylate acid esters, diene polymers, polyalkyl styrenes, alkenyl aryl conjugated diene copolymers, polyolefins and multifunctional viscosity improvers such as dispersant viscosity improvers.

Pour point depressants are a diverse group of materials which serve to reduce the pour point of a wax-containing oil. Typical pour point depressants include alkylated wax naphthalenes, polymethacrylates, alkylated wax phenols, styrene-based polyesters, and vinyl acetate copolymers. See for example, page 8 of "Lubricant Additives" by C. V. Smalheer and R. Kennedy Smith (Lesius-Hiles Company Publishers, Cleveland, Ohio, 1967).

Antioxidants are used to retard degradation and thickening of oil due to oxidation. They include phenate sulfides, phosphosulfurized terpenes, aromatic amines, sulfurized esters, and hindered phenols.

Rust inhibitors include alkenylsuccinic acids, substituted imidazolines, amine phosphates, and alkylated phenoxy alkylene oxides.

Anticorrosion agents include additives which react chemically with non-ferrous metal components and include organic phosphites, zinc diorgano-dithiophosphates, metal carbamates sulfurzed terpenes and phosphosulfurized terpenes.

Antiwear agents include sulfurized olefins, sulfurized esters such as sulfurized fatty oils, hydrocarbyl phosphates or thiophosphates, phosphorus-containing amides, zinc dialkyldithiophosphates and dithiocarbamates.

These and other additives are described in greater detail in U.S. Pat. No. 4,582,618 (column 14, line 52 through column 17, line 16, inclusive) and in Smalheer, "Lubricant Additives," Lezius-Hiles Co., Cleveland, 1967.

In addition to use in passenger car motor oils, the dispersants of the present invention can also be used in other types of lubricants generally, including gear oil lubricants, automatic transmission fluids, manual transmission fluids, power steering fluids, hydraulic fluids, and metal-working fluids.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic sites of other molecules. The products formed thereby, including the products formed upon employing the composition of the present invention in its intended use, may not susceptible of easy description. Nevertheless, all such modifications and reaction, products are included within the scope of the present invention; the present invention encompasses the composition prepared by admixing the components described above.

EXAMPLES 1–3

Three samples of lubricant are prepared, in oil of lubricating viscosity, containing the dispersant of Example B, above, at a level of about 4% by weight (inclusive of diluent oil), so as to contain 0.05% by weight molybdenum. The three samples contain an alkenyl ester sulfide antioxidant/antiwear agent in amounts of 0.6%, 1.2%, and 1.8%, respectively (inclusive of about 5% diluent oil).

Each of the three samples is subjected to a friction test. The test involves placing a small (0.2 mL) oil sample onto a flat, steel test coupon. The flat coupon is placed into a test apparatus and heated to 40° C. A cylindrical specimen is similarly mounted in the test apparatus. The cylinder rests on the oil-coated surface of the flat specimen. The system is set to run at 400N load, 50 Hz frequency, 1.0 mm stroke length for approximately 45 minutes. The temperature of the specimen and oil is ramped from 40–120° C. in 5 minute stages over the test duration. The friction coefficient is recorded throughout the test. The friction coefficient from 100 to 120° C. and at 110° C. is averaged to determine the oil's performance. Poor oils display higher friction coefficients.

The results of the test provide friction coefficient values for the samples of 0.073, 0.078, and 0.088, respectively.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives; and other such materials which are normally understood to be present in the commercial grade. However, the amount of each chemical component is presented exclusive of any solvent or diluent oil which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A molybdated dispersant composition prepared by reacting phosphoric acid or silicic acid, MoO$_3$, and an amine-containing dispersant, wherein the amine-containing dispersant comprises a polyamine moiety and a hydrocarbyl moiety having a molecular weight of about 500 to about 5000.

2. The molybdated dispersant composition of claim 1 wherein the molybdenum atoms in the reaction product thus formed are predominantly in the +6 oxidation state.

3. The molybdated dispersant composition of claim 1 wherein said molybdated dispersant composition is represented by the formula:

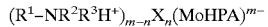

wherein R$^1$—NR$^2$R$^3$ represents the amine-containing dispersant, R$^1$ is a group providing dispersant properties to said dispersant composition, each of R$^2$ and R$^3$ is independently hydrogen, a hydrocarbyl group, or an additional R$^1$ group; X is hydrogen, a monovalent metal ion, a single valence of a polyvalent metal ion, an ammonium ion, or an amine cation, m is 3 or 4, n is 0 to about 2.5 when m is 3 and 0 to about 3.5 when m is 4, and (MoHPA)$^{m-}$ is a molybdenum heteropolyacid anion of charge m.

4. A molybdated dispersant composition represented by the formula:

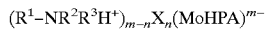

wherein R$^1$—NR$^2$R$^3$ represents a dispersant, R$^1$ is a group providing dispersant properties to said dispersant composition, each of R$^2$ and R$^3$ is independently hydrogen, a hydrocarbyl group, or an additional R$^1$ group; wherein the dispersant comprises a polyamine moiety and a hydrocarbyl moiety having a molecular weight of about 500 to about 5000; X is hydrogen, a monovalent metal ion, a single valence of a polyvalent metal ion, an ammonium ion, or an amine cation, m is 3 or 4, n is 0 to about 2.5 when m is 3 and 0 to about 3.5 when m is 4, and (MoHPA)$^{m-}$ is a molybdenum heteropolyacid anion of charge m.

5. A molybdated dispersant composition represented by the formula:

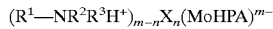

wherein R$^1$—NR$^2$R$^3$ represents a dispersant, R$^1$ is a group providing dispersant properties to said dispersant composition and wherein R$^1$ contains at least one amine group, each of R$^2$ and R$^3$ is independently hydrogen, a hydrocarbyl group, or an additional R$^1$ group; X is hydrogen, a monovalent metal ion, a single valence of a polyvalent metal ion, an ammonium ion, or an amine cation, m is 3 or 4, n is 0 to about 2.5 when m is 3 and 0 to about 3.5 when m is 4, and (MoHPA)$^{m-}$ is a molybdenum heteropolyacid anion of charge m.

6. The composition of claim 5 wherein an amine group within R$^1$ is in the form of a salt with a molybdenum heteropolyacid anion.

7. A molybdated dispersant composition represented by the formula:

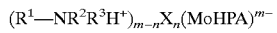

wherein R$^1$—NR$^2$R$^3$ represents a dispersant, R$^1$ is a group providing dispersant properties to said dispersant composition, each of R$^2$ and R$^3$ is independently hydrogen, a hydrocarbyl group, or an additional R$^1$ group; X is hydrogen, a monovalent metal ion, a single valence of a polyvalent metal ion, an ammonium ion, or an amine cation, m is 3 or 4, n is 0 to about 2.5 when m is 3 and 0 to about 3.5 when m is 4, and (MoHPA)$^{m-}$ is a molybdenum heteropolyacid anion of charge m; wherein the R$^1$—NR$^2$R$^3$ moiety is a succinimide dispersant or a Mannich dispersant.

8. The composition of claim 7 wherein the dispersant is the reaction product of a hydrocarbyl-substituted succinic anhydride or reactive equivalent thereof with a polyethylene polyamine.

9. The composition of claim 8 wherein the hydrocarbyl substituent is a polymer of isobutylene having a number average molecular weight of about 500 to about 5000.

10. The composition of claim 9 wherein the substituent has a number average molecular weight of about 900 to about 3500.

11. The composition of claim 8 wherein the mole ratio of carbonyl groups to nitrogen atoms in the succinimide dispersant is about 0.4:1 to about 1.5:1.

12. The composition of claim 8 wherein the mole ratio of carbonyl groups to nitrogen atoms in the succinimide dispersant is about 0.7:1 to about 1.4:1.

13. The composition of claim 4 wherein n is 0.

14. The composition of claim 4 wherein (MoHPA)$^{m-}$ is a silicomolybdate and m is 4.

15. The composition of claim 4 wherein (MoHPA)$^{m-}$ is a phosphomolybdate and m is 3.

16. The composition of claim 4 wherein (MoHPA)$^{m-}$ is PMo$_{12}$O$_{40}$$^{3-}$.

17. A process for preparing a molybdated composition comprising reacting phosphoric acid or silicic acid with MoO$_3$ and with an amine, wherein the amine is an amine-containing dispersant comprising a polyamine moiety and a hydrocarbyl moiety having a molecular weight of about 500 to about 5000.

18. The process of claim 17 wherein the reaction is conducted in an inert medium in the presence of at least a catalytic amount of water.

19. The process of claim 18 wherein the inert medium is a diluent oil.

20. A process for preparing a molybdated composition comprising reacting phosphoric acid or silicic acid with MoO$_3$ and with an amine in a diluent oil in the presence of at least a catalytic amount of water, wherein the reaction is initially conducted at a temperature at or below the boiling point of water, and thereafter the temperature is raised to above the boiling point of water, whereby said water is removed from the reaction mixture.

21. The process of claim 20 wherein said initial reaction is conducted at a temperature of about 80 to about 98° C. for about 0.5 to about 24 hours, and thereafter the temperature is raised to about 120 to about 180° C.

22. A process for preparing a molybdated composition comprising reacting phosphoric acid or silicic acid with MoO$_3$ and with an amine-containing dispersant.

23. A process for preparing a molybdated dispersant comprising reacting an amine-containing dispersant which comprises a polyamine moiety and a hydrocarbyl moiety having a molecular weight of about 500 to about 5000, with a molybdenum heteropoly acid or a partially neutralized equivalent thereof to form a salt thereof.

24. The process of claim 23 wherein the molybdenum heteropolyacid is a phosphomolybdate or a silicomolybdate.

25. The process of claim 23 wherein the molybdenum heteropolyacid is H$_3$PMo$_{12}$O$_{40}$.

26. A process for preparing a molybdated dispersant comprising reacting an amine-containing dispersant with a molybdenum heteropoly acid or a partially neutralized equivalent thereof to form a salt thereof, wherein the molybdenum heteropoly acid or partially neutralized equivalent thereof is supplied as a solution in an alkanol containing up to about 4 carbon atoms.

27. The process of claim 26 wherein the alkanol comprises methanol.

28. A process for preparing a molybdated composition comprising reacting phosphoric acid or silicic acid with $MoO_3$ and with an amine-containing dispersant, without isolation of an intermediate molybdenum heteropoly acid.

29. The process of claim 28 wherein the phosphoric acid or silicic acid, the $MoO_3$, and the amine-containing dispersant are reacted by mixing said materials in an inert medium in the presence of a catalytic amount of water.

* * * * *